US012590951B2

(12) United States Patent
Liu et al.

(10) Patent No.: US 12,590,951 B2
(45) Date of Patent: Mar. 31, 2026

(54) CULTURE MEDIUM AND CULTURE METHOD FOR PRIMARY CELLS OF INTESTINAL CANCER

(71) Applicant: PRECEDO PHARMACEUTICALS CO., LTD, Anhui (CN)

(72) Inventors: Qingsong Liu, Anhui (CN); Yuying He, Anhui (CN); Cheng Chen, Anhui (CN); Tao Huang, Anhui (CN); Tao Ren, Anhui (CN); Wenchao Wang, Anhui (CN); Li Wang, Anhui (CN)

(73) Assignee: PRECEDO PHARMACEUTICALS CO., LTD, Hefei (CN)

( * ) Notice: Subject to any disclaimer, the term of this patent is extended or adjusted under 35 U.S.C. 154(b) by 345 days.

(21) Appl. No.: 18/275,125

(22) PCT Filed: Feb. 5, 2021

(86) PCT No.: PCT/CN2021/075366
§ 371 (c)(1),
(2) Date: Jul. 31, 2023

(87) PCT Pub. No.: WO2022/160368
PCT Pub. Date: Aug. 4, 2022

(65) Prior Publication Data
US 2024/0319170 A1      Sep. 26, 2024

(30) Foreign Application Priority Data
Feb. 1, 2021      (CN) .......................... 202110134946.7

(51) Int. Cl.
*G01N 33/50* (2006.01)
*C12N 5/09* (2010.01)

(52) U.S. Cl.
CPC ....... *G01N 33/5011* (2013.01); *C12N 5/0693* (2013.01); *C12N 2500/02* (2013.01); *C12N 2501/01* (2013.01); *C12N 2501/105* (2013.01); *C12N 2501/11* (2013.01); *C12N 2501/115* (2013.01); *C12N 2501/117* (2013.01); *C12N 2501/119* (2013.01); *C12N 2501/12* (2013.01); *C12N 2501/2322* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 2013/0309681 A1 | 11/2013 | Schlegel et al. | |
| 2019/0085297 A1* | 3/2019 | Chen ................... | C12N 5/0693 |
| 2020/0071676 A1 | 3/2020 | Kakinuma et al. | |
| 2020/0172861 A1 | 6/2020 | Ortega et al. | |

FOREIGN PATENT DOCUMENTS

| | | |
|---|---|---|
| CN | 101353646 A | 1/2009 |
| CN | 106011071 A | 10/2016 |
| CN | 107988162 A | 5/2018 |
| CN | 110592018 A | 12/2019 |
| CN | 110592020 A | 12/2019 |
| CN | 111394314 A | 7/2020 |
| CN | 111808815 A | 10/2020 |
| CN | 111808816 A | 10/2020 |
| RU | 2 709 378 C1 | 12/2019 |
| WO | 2017156341 A1 | 9/2017 |
| WO | 2017/199811 A1 | 11/2017 |
| WO | 2018/090375 A1 | 5/2018 |
| WO | 2019/006127 A1 | 1/2019 |
| WO | 2020/072506 A1 | 4/2020 |
| WO | 2020/206999 A1 | 10/2020 |

OTHER PUBLICATIONS

Trukhan I.S., "The Culture Medium as a Key Factor of the Mammalian Cell Cultivation", International Journal of Applied and Fundamental Research 12(1):165-172 (2018), together with an English-language abstract.
Chinese Office Action dated Sep. 6, 2023 received in Chinese Application No. 202110134946.7, together with an English-language translation.
Russian Office Action dated Apr. 23, 2024 received in Russian Application No. 2023119075/10(041115), together with an English-language translation.
International Search Report dated Aug. 6, 2021 issued in PCT /CN2021/075366.
He, Shuangwu et al. "Effects of Gastrin on Proliferation of Primary Cultured Cancer Cells of Human Large Intestine", Chinese Journal of Bases and Clinics in General Surgery (May 31, 1998), vol. 5, No. 3, with English Abstract.
Liu, Jie et al. "Effect of Insulin-like Growth Factor-I on Apoptosis of Colon Cancer Cell Through Signaling Pathway of PI-3K/Akt*", Progress in Modern Biomedicine (Mar. 6, 2011), vol. 11, No. 6, pp. 1078-1082, with English Abstract.

(Continued)

*Primary Examiner* — Blaine Lankford
(74) *Attorney, Agent, or Firm* — Scully, Scott, Murphy & Presser, P.c.

(57) ABSTRACT

Disclosed are a culture medium and a culture method for in vitro expansion of primary cells of intestinal cancer. The culture medium comprises an initial culture medium, a Rho protease inhibitor, an antibiotic, gastrin, A8301, a non-essential amino acid, cholera toxin, an insulin-like growth factor-1, nicotinamide, insulin, fetal bovine serum, and an additive selected from at least one of a B27 additive and an N2 additive. By using the culture medium, effective and rapid expansion of the primary cells of intestinal cancer can be achieved. The expanded cells maintain the pathological characteristics of patients, and the culture success rate and the cell expansion rate of the primary cells of intestinal cancer are improved, which provide a research foundation for personalized treatment of the patients.

14 Claims, 7 Drawing Sheets

(56)          References Cited

OTHER PUBLICATIONS

Japanese Notice of Reasons for Refusal dated Oct. 1, 2024 received in Japanese Patent Application No. 2023-546220, together with an English-language translation.

Liu X. et al., "Conditional Reprogramming and Long-Term Expansion of Normal and Tumor Cells from Human Biospecimens", Nature Protocols 12(2):439-451 (2017), cited in Extended EPO SR.

Extended European Search Report dated Dec. 10, 2024 received in European Application No. 21 921 968.0.

* cited by examiner (A)                                                    (B)

(C)                                                    (D)

(A) OE(E)019 5 days (B) OE(E)028 14 days (C) OE(E)021 3 days (D) OE(E)023 9 days (E) OE(E)026   6 days (F) OE(E)025   4 days (G) OE(E)024   4 days (H) OE(E)004   7 days (A) Ki-67 20x                    (B) CK20   20x (C) CDX-2 20X                    (D) Villin 20x （A）Ki-67 20x （B）CK20   20x

（C）CDX-2 20X

（D）Villin 20x

OE (O)001

(A)          (B)

(A)

(B)

CULTURE MEDIUM AND CULTURE METHOD FOR PRIMARY CELLS OF INTESTINAL CANCER

TECHNICAL FIELD

The invention relates to the field of biotechnology, in particular to a culture medium and a culture method for rapid expansion of primary cells of intestinal cancer, and their uses in efficacy evaluating and screening of drugs.

BACKGROUND OF THE INVENTION

Intestinal cancer is a disease caused by the interaction of genetic and environmental factors, and it is one of the most common gastrointestinal tumors worldwide. Survey data (Shu Zheng et al., Prevention of Colorectal Cancer, Chinese Journal of Oncology, 2004, vol. 13, NO. 1, pp 1-2) show that intestinal cancer is one of the most common tumors, and the overall incidence rate and mortality rate are both on the rise, which makes it a malignant tumor that seriously threatens life and health. Surgery combined with postoperative chemotherapy is currently the main treatment for intestinal cancer. Although surgical techniques have improved in recent years which lead to the improvement of survival rate of intestinal cancer patients, metastasis and recurrence of tumor still bring adverse prognosis to patients. In terms of precise treatment of colorectal cancer, the emergence of targeted drugs has brought hope to patients with advanced colorectal cancer, and the future development is how to rationally select targeted drugs and formulate individualized treatment plans. The continuous innovation of drug sensitivity testing technology provides strong technical supports for the prediction of the efficacy of targeted drugs, chemotherapy drugs, and targeted drug combinations, and lays a solid foundation for the realization of individualized treatment of patients with intestinal cancer.

Existing intestinal cancer cell lines cultured in vitro are mainly obtained through long-term culture of normal cells to spontaneously immortalize or transfect oncogenes that promote the immortalization of normal cells. The cell lines established by traditional methods remain a mainstay of cellular, molecular, and cancer biology researches. However, these methods change the genetic background of cells, and long-term cultured cell lines are also prone to genome instability, which may lead to artificial changes in the phenotype of tumor cell lines and tumor cells in vivo. These cell lines usually lack the complex heterogeneity of the primary tumor, which limits the application of these cell lines for predicting tumor cell response and affects the accuracy of scientific research and drug development of intestinal cancer. In addition, in the process of culturing cells obtained from intestinal cancer tissues into cancer cells, it is difficult to obtain cancer cells by conventional culture methods, and there are problems in the culture process, such as interference by fibroblasts, the clones formed cannot be subcultured, which limits the application of human primary cells of intestinal cancer.

In 2017, Xuefeng Liu et al. used irradiated mouse fibroblasts and a Rho-associated kinase inhibitor (Y-27632) to expand epithelial-derived cells. This system has the ability to achieve unlimited growth of epithelial-derived cells without genetic manipulation (Xuefeng Liu et al., Conditional reprogramming and long-term expansion of normal and tumor cells from human biospecimens. *Nat. Protoc.* 2017, 12, 439). However, the method established by Xuefeng Liu et al. has a long culture period and cannot achieve rapid cell expansion, which also limits the application of this technology.

SUMMARY OF THE INVENTION

In order to solve the above-mentioned technical problems, the invention provides a culture medium and a culture method for rapid expansion of primary cells of intestinal cancer in vitro.

One aspect of the invention is to provide a culture medium for primary cells of intestinal cancer, comprising an initial culture medium, a Rho protease inhibitor, an antibiotic, gastrin, A8301, a non-essential amino acid, cholera toxin, insulin-like growth factor-1, nicotinamide, insulin, fetal bovine serum, and an additive selected from at least one of a B27 additive and an N2 additive. The initial medium is selected from the group consisting of DMEM/F12, DMEM, F12 or RPMI-1640.

Preferred embodiments of the invention include at least one of the following aspects:

(1) the Rho protease inhibitor is one or more selected from the group consisting of Y27632, fasudil, and H-1152, preferably Y27632, and the concentration is preferably 2.5-40 μM, more preferably 2.5-5 μM, most preferably 5 μM;

(2) the antibiotic is one or more selected from the group consisting of streptomycin/penicillin, amphotericin B and Primocin, in case of streptomycin/penicillin, with streptomycin having a concentration within the range of 25-400 μg/mL, preferably 50-200 μg/mL, more preferably 200 μg/mL, with penicillin having a concentration within the range of 25-400 U/mL, preferably 50-200 U/mL, more preferably 200 U/mL; in case of amphotericin B, having a concentration within the range of 0.25-4 μg/mL, preferably 0.5-2 μg/mL; and in case of Primocin, having a concentration within the range of 25-400 μg/mL, preferably 50-200 μg/mL;

(3) the concentration range of gastrin is preferably 1.25-20 nM, more preferably 2.5-10 nM, most preferably 5 nM;

(4) the concentration range of A8301 is preferably 25-200 nM, more preferably 200 nM;

(5) the non-essential amino acid is one or more selected from the group consisting of glycine, alanine, asparagine, aspartic acid, glutamic acid, proline and serine, and the total concentration range of non-essential amino acids is 25-400 μM, more preferably 50 μM;

(6) the concentration range of cholera toxin is preferably 1.25-20 ng/mL, more preferably 2.5-5 ng/mL, most preferably 5 ng/mL;

(7) the concentration range of insulin-like growth factor-1 is preferably 5-405 ng/mL, more preferably 45 ng/mL;

(8) the concentration range of nicotinamide is preferably 2-8 mM, more preferably 4-8 mM, most preferably 4 mM;

(9) the concentration range of insulin is preferably 0.5-4 μg/mL, more preferably 1-2 μg/mL, most preferably 2 μg/mL;

(10) the volume ratio of fetal bovine serum relative to the culture medium is preferably 2.5% (v/v)-5% (v/v), more preferably 5% (v/v);

(11) the volume ratio of B27 or N2 additive to the culture medium is preferably 1:25-1:200, more preferably 1:25-1:50, and most preferably 1:25.

The invention also provides a culture method for primary cells of intestinal cancer. In the culture method for primary cells of intestinal cancer of the invention, the primary cells of intestinal cancer are cultured using the culture medium for primary cells of intestinal cancer of the invention.

The culture method for primary cells of intestinal cancer of the invention comprises the following steps:

1. Isolation of Primary Cells of Intestinal Cancer (1) After being rinsed with washing medium, tissue samples, endoscopic samples are added with washing medium and tissue digestion solution (the amount of tissue digestion solution added is about 5-10 mL tissue digestion solution for 1 g of tumor tissue) at a ratio of 1:3, and placed in a constant-temperature shaker for digestion, at a digestion temperature ranges from 4 to 37° C., preferably 37° C.; the rotation rate for digestion ranges from 200 rpm to 350 rpm, preferably 300 rpm;

(2) the digestion can be terminated until no obvious tissue mass remained, and the digestion time ranges from 3 to 6 hours, preferably 4 hours;

(3) the supernatant is discarded after centrifugation with a centrifugation speed ranging from 1200 to 1600 rpm, preferably 1500 rpm, the centrifugation time ranging from 2 to 6 minutes, preferably 4 minutes; the resultant is resuspended with the addition of DMEM/F12 medium containing 10% serum.

2. Culturing Using the Culture Medium for Primary Cells of Intestinal Cancer of the Invention The primary cells of intestinal cancer obtained in the above step 1 are resuspended with the culture medium for primary cells of intestinal cancer of the invention and counted, which are inoculated into a culture dish at a cell density of $1 \text{-} 10 \times 10^4$ cells/cm$^2$; at the same time, trophoblast cells are added at a cell density of $2 \text{-} 3 \times 10^4$ cells/cm$^2$; the cells are digested for passaging after the cells grow to cover 90% or more of the culture dish.

Specifically, the formulation of the washing medium described in step 1 is: DMEM/F12 medium containing 100 μg/mL Primocin (purchased from InvivoGen, 0.2% (v/v), the concentration of the commercial product is 50 mg/ml); the formulation of the tissue digestion solution described in step 1 is: 1640 medium (Corning, 10-040-CVR), collagenase II (2 mg/mL), collagenase IV (2 mg/mL), DNase (50 U/mL), hyaluronidase (0.75 mg/mL), calcium chloride (3.3 mM), BSA (10 mg/mL); the trophoblast cells described in step 2 is, for example, irradiated NIH-3T3 cells, and the irradiation source is X-ray or γ-ray, preferably γ-ray, with a radiation dose of 20-50 Gy, preferably 30 Gy.

The invention also provides a method for screening drugs for intestinal cancer, comprising the following steps:

(1) culturing primary cells of intestinal cancer for drug screening, by using the culture method for primary cells of intestinal cancer of the invention;

(2) selecting a drug to be tested and diluting the drug based on the required concentration gradients;

(3) adding the drug in various concentration gradients to the cells cultured and obtained in step (1);

(4) detecting the cell viability.

The technical solution of the invention can produce the following technical effects:

(1) the success rate for culturing the primary cells of intestinal cancer can be improved, with a success rate of 80% or more;

(2) the primary cells of intestinal cancer cultured in vitro can maintain the pathological characteristics of patients;

(3) the primary cells of intestinal cancer cultured are not interfered by mesenchymal cells such as fibroblasts and adipocytes;

(4) the primary cells of intestinal cancer can be expanded with high efficiency, with a magnitude of $10^6$ of cells being successfully expanded within about one week from the starting of $10^5$-level cell number, and the expanded primary cells of intestinal cancer have the ability of continuous passage;

(5) the cost for culture is controllable, as the culture medium does not require expensive Wnt agonists, R-spondin family proteins, BMP inhibitors, FGF10 and the like factors;

(6) this technology can culture and provide the primary cells of intestinal cancer with large quantity and high uniformity, which is suitable for high-throughput screening of new candidate compounds and high-throughput drug sensitivity functional tests in vitro for patients.

DETAILED DESCRIPTION OF THE INVENTION

Figure 1:
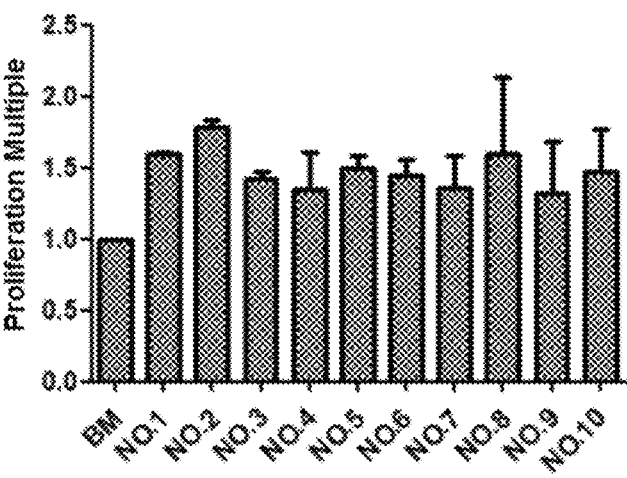
FIG. 1 is a graph showing the effects of combinations of different factors added in the culture medium for primary cells of intestinal cancer on the proliferation of primary cells of intestinal cancer.
Figure 2:
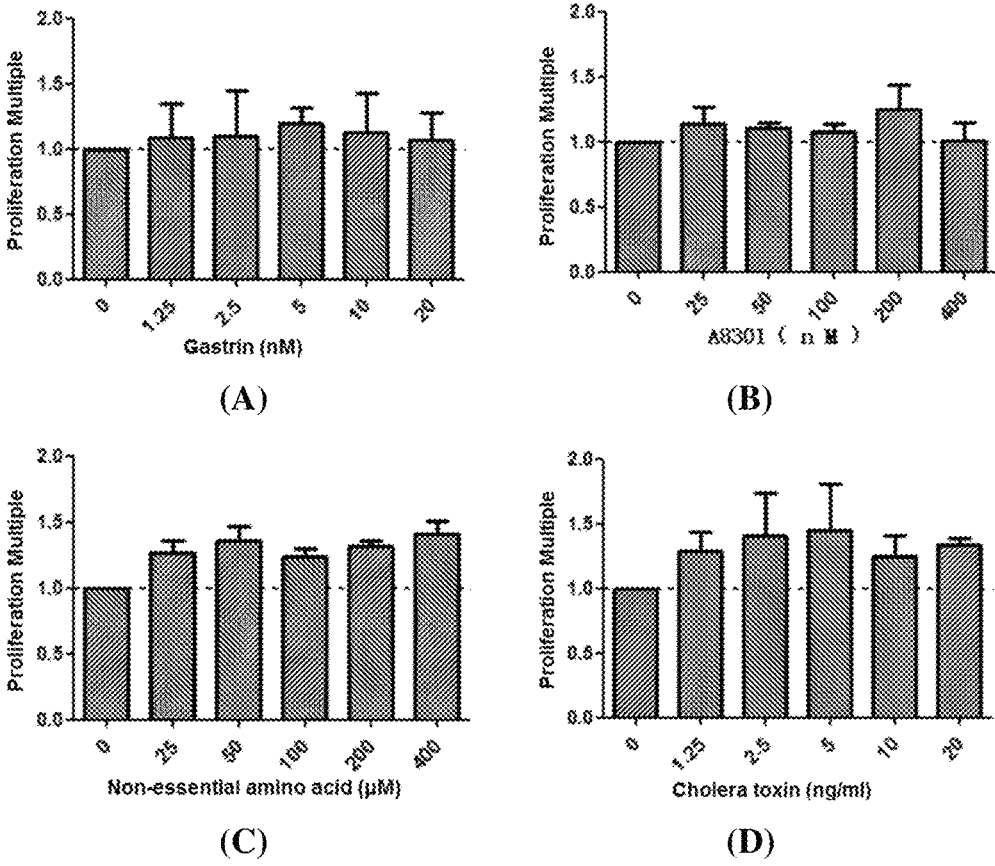
FIGS. 2A to 2J are graphs showing the effects of different concentrations of factors added to the culture medium for primary cells of intestinal cancer of the invention on culture of the primary cells of intestinal cancer.
Figure 2:
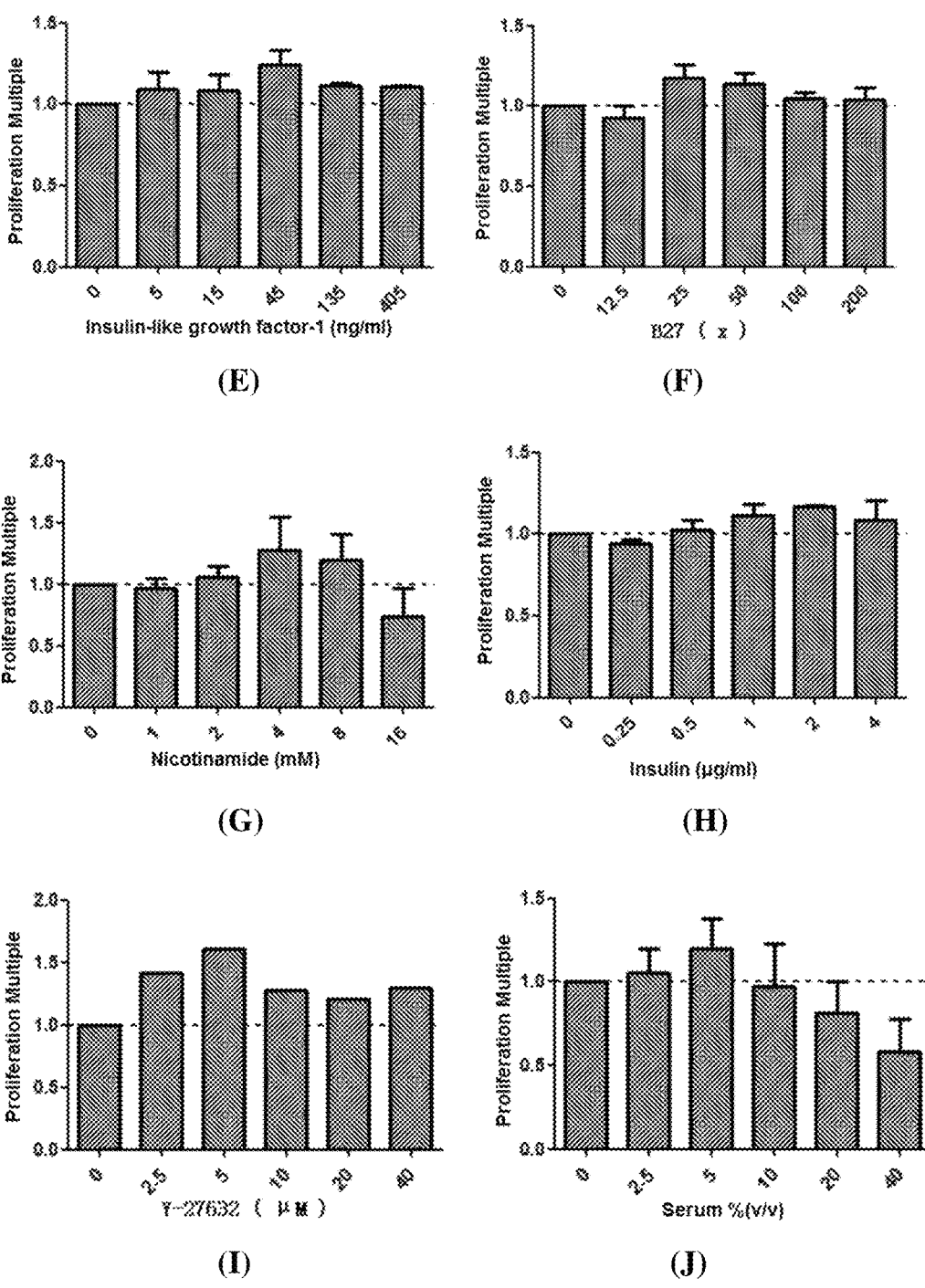
Figure 3:
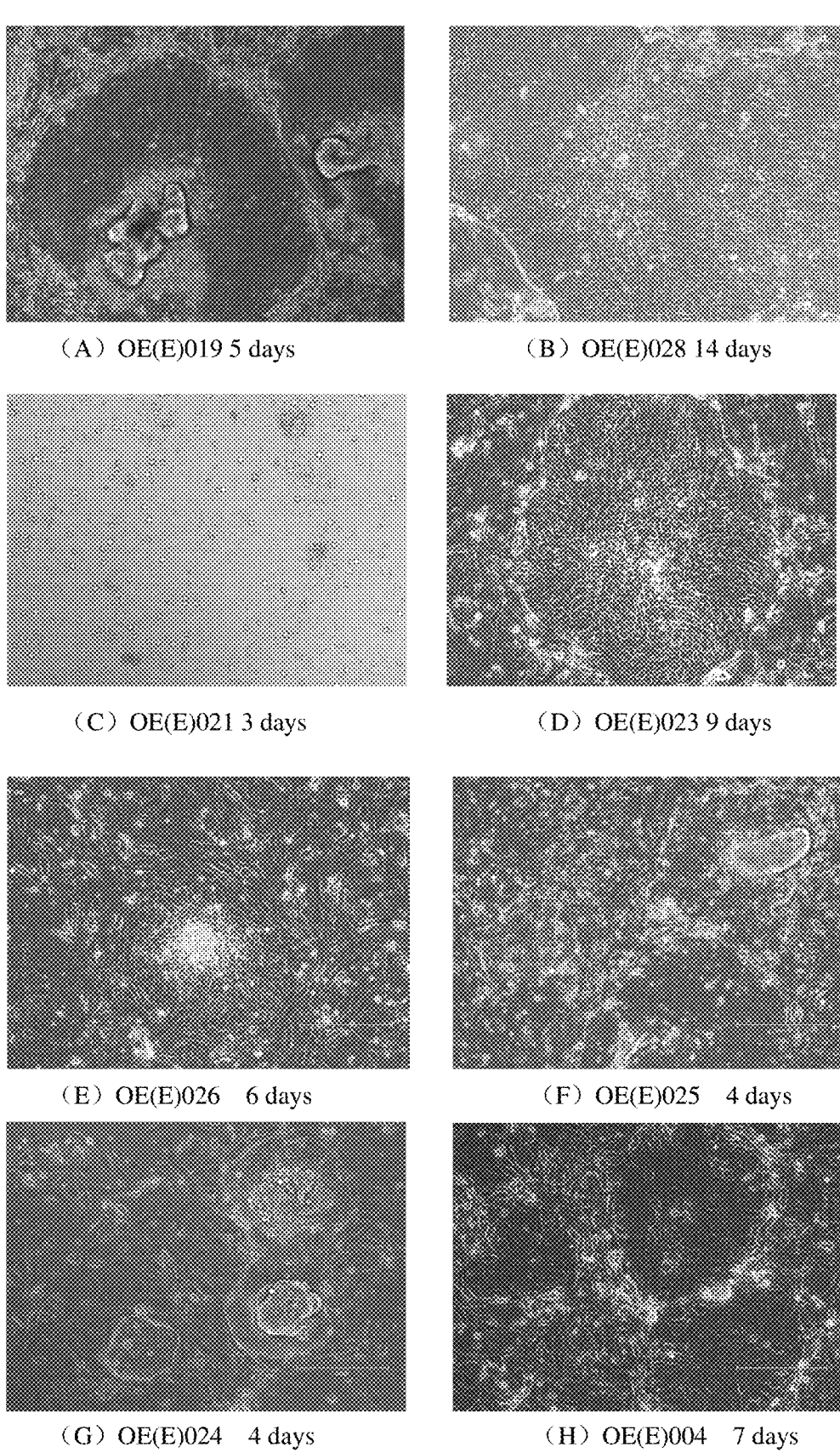
FIGS. 3A to 3H shows the photos of primary cells of intestinal cancer obtained by culturing with the culture medium for primary cells of intestinal cancer of the invention by observing with a microscope.

In order to better understand the invention, it is further described below in combination with the embodiments and the drawings. The following examples are provided only for the purpose of illustrating, but not for limiting the invention.

Example 1. Effect of Respective Factors Added to the Culture Medium for Primary Cells of Intestinal Cancer on the Proliferation of Primary Cells of Intestinal Cancer (1) Preparation of Culture Medium for Primary Cells of Intestinal Cancer First, Basic Medium was prepared. The formulation of Basic Medium is: DMEM/F12 medium (purchased from Corning)+5 μM Y27632 (purchased from MCE)+5% (v/v) fetal bovine serum (purchased from Excell Bio)+100 μg/mL Primocin (purchased from InvivoGen, 0.2% (v/v), the concentration of commercial product is 50 mg/ml).

Different types of additives (see Table 1) were added to the Basic Medium to prepare the culture mediums for primary cells of intestinal cancer containing different components.

(2) Isolation and Treatment of Primary Cells of Intestinal Cancer

1. Sample Selection

Tissue samples (intraoperative/endoscopic) of intestinal cancer solid tumors were obtained from patients by professional medical practitioner of professional medical institutions, and all patients have signed the informed consent. Intraoperative samples had the size of 0.25 cm$^3$, and endoscopic samples had the size of 0.025 cm$^3$; commercial tissue preservation solution (manufacturer: Miltenyi Biotec) was used for storage and transportation.

2. Material Preparation

After subjecting to surface sterilization, 15 mL sterile centrifuge tubes, pipettors, 10 mL pipettes, sterile pipette tips, etc., were put in an ultra-clean workbench for ultraviolet irradiation of 30 minutes. The washing medium was taken out from a 4° C. refrigerator 30 minutes in advance, and the tissue digestion solution was taken out from a –20° C. refrigerator 30 minutes in advance.

Washing medium: DMEM/F12 medium containing 100 μg/mL Primocin (purchased from InvivoGen, 0.2% (v/v), the concentration of commercial product is 50 mg/ml).

Tissue digestion solution: 1640 medium (Corning, 10-040-CVR), collagenase II (2 mg/mL), collagenase IV (2 mg/mL), DNase (50 U/mL), hyaluronidase (0.75 mg/mL), calcium chloride (3.3 mM), BSA (10 mg/mL).

Collagenase II, collagenase IV, DNase, and hyaluronidase mentioned above were all purchased from Sigma Corporation; calcium chloride was purchased from Sangon Biotech (Shanghai) Co., Ltd.; BSA was purchased from Biofroxx Corporation.

3. Sample Isolation 3.1. Tissue samples were transferred from the ultra-clean workbench to a culture dish, and the tissue with blood was removed. The tissue samples were rinsed twice with washing medium, and then were transferred to another culture dish and mechanically cut with a sterile scalpel into tissue blocks of 1×1×1 mm$^3$ in size.

3.2. The cut intraoperative or endoscopic tissues were aspirated into a 15 mL centrifuge tube, to which 5 mL of washing medium was added, fully mixed, and then centrifuged at 1500 rpm for 4 minutes.

3.3. The supernatant was discarded, and the resultant was added with 1:3 mixture of washing medium and tissue digestion solution (the amount of tissue digestion solution added was about 10 mL tissue digestion solution for 1 g of tumor tissue). The samples were marked with names and numbers, sealed with sealing film, and then digested in a shaker (Zhichu Instrument ZQLY-180N) at 37° C., 300 rpm. The completion of digestion was determined via observation every 30 minutes, based on the existing of visible particles or not. The digestion time was 4 hours.

3.4. After the digestion was completed, undigested tissue mass was filtered out through a 100 μM filter mash. The tissue mass on the filter mash was rinsed into the centrifuge tube with washing medium to reduce cell loss. The resultant was centrifuged at 25° C., 1500 rpm for 4 minutes.

3.5. The supernatant was discarded and the resultant was observed to determine whether there were blood cells. If there were blood cells, 8 mL blood cell lysate (Sigma) was added in the resultant and fully mixed, lysed at 4° C. for 20 minutes, with inverting and mixing once during the process. The resultant was centrifuged at 25° C., 1500 rpm for 4 minutes.

3.6. The supernatant was discarded and 2 mL DMEM/F12 medium containing 10% serum (Excell Bio, FND500) was added to resuspend the cells for reserve.

4. Cell Count and Treatment 4.1 Microscopic observation: a small amount of resuspended cells were plated in a culture dish, and the density and morphology of cancer cells were observed under a microscope (CNOPTEC, BDS400);

4.2 Viable cell counting: 12 μL of the resuspended cell suspension was fully mixed with 12 μL of trypan blue staining solution (Sangon Biotech (Shanghai) Co., Ltd.), and then 20 μL of the mixture was added into a cell counting plate (Countstar, specifications: 50 pieces/box). The percentage of viable large cells (cell size >10 μm)=number of viable cells/number of total cells×100%, was calculated with a cell counter (Countstar, IC1000).

(3) Culture of Primary Cells of Intestinal Cancer

The culture mediums of different components as shown in Table 1 were added into a 48-well plate at a volume of 1 mL/well. Primary cells of intestinal cancer isolated from two cases of intestinal cancer tissues (numbered OE0042 and OE(E)003) according to the above step (2) were inoculated into the 48-well culture plate at a cell density of 3×10$^4$ cells/well, and were cultured at 37° C., under 5% CO$_2$ concentration. After culturing for 7-10 days, when the cells grew to 85%, the culture medium was discarded, and 100 μL/well of 0.05% trypsin (purchased from Gibco) was used to rinse the cells once. After the trypsin was removed, 200 μL of 0.05% trypsin was added to each well. The plate was then placed in a 37° C., 5% CO$_2$ incubator for 10 minutes, and the cells were observed under a microscope (CNOPTEC, BDS400), showing that the cells had completely digested. 300 μL of DMEM/F12 medium containing 10% serum (Excell Bio, FND500) was added to stop the digestion. 20 μL of the resultant was added into a cell counting plate (Countstar, specification: 50 pieces/box), and the total number of cells was counted with a cell counter (Countstar, IC1000). Specifically, Basic Medium without any additives was used as an experimental control, and the experimental results are shown in Table 1.

TABLE 1

| No. | Types of medium additive | Supplier | Final concentration | Level of promoting cell proliferation |
|---|---|---|---|---|
| 1 | N2 | Gibco | 1:25 | + |
| 2 | epidermal growth factor | R&D | 5 ng/mL | o |
| 3 | hepatocyte growth factor | Peprotech | 10 ng/mL | o |
| 4 | basic fibroblast growth factor | R&D | 5 ng/mL | – |
| 5 | R-spondin1 | R&D | 20 ng/mL | o |
| 6 | prostaglandin E2 | Tocris | 0.5 μM | – |
| 7 | insulin | Peprotech | 1 ug/mL | + |
| 8 | IL-22 | Peprotech | 20 ng/mL | – |
| 9 | B27 | Gibco | 1:25 | + |
| 10 | A8301 | MCE | 100 nM | – |
| 11 | SB202190 | MCE | 200 nM | o |

TABLE 1-continued

| No. | Types of medium additive | Supplier | Final concentration | Level of promoting cell proliferation |
|-----|---------|----------|---------------------|---------------------|
| 12 | nicotinamide | Sigma | 4 mM | + |
| 13 | glutamine | GIBCO | 1:20 | – |
| 14 | cholera toxin | Sigma | 5 ng/mL | + |
| 15 | hydrocortisone | Sigma | 10 ng/mL | o |
| 16 | Noggin | R&D | 30 ng/mL | o |
| 17 | insulin-like growth factor-1 | R&D | 45 ng/mL | + |
| 18 | gastrin | MCE | 5 nM | o |
| 19 | KGF | R&D | 5 ng/mL | o |
| 20 | non-essential amino acids | Corning | 50 μM | + |
| 21 | TGF-β1 | R&D | 2 ng/mL | – |
| 22 | FGF10 | sino biological | 1 ng/mL | – |

Wherein, "+" indicates that compared with the Basic Medium, the medium added with the additive(s) has the effect of promoting the proliferation of primary cells of intestinal cancer isolated from intestinal cancer tissue in at least two cases; "–" indicates that the medium added with the additive(s) has the effect of inhibiting the proliferation of primary cells of intestinal cancer isolated from intestinal cancer tissue in at least one case; "o" indicates that the medium added with the additive(s) has no significant effect on the proliferation of primary cells of intestinal cancer isolated from intestinal cancer tissue in at least two cases.

According to the above results, factors including non-essential amino acid, cholera toxin, insulin-like growth factor-1, B27 or N2, nicotinamide, insulin, prostaglandin E2, A8301 and gastrin were selected for further experiments of culture.

Example 2. Effects of the Combinations of Different Factors Added in the Culture Medium of Primary Cells of Intestinal Cancer on the Proliferation of Primary Cells of Intestinal Cancer According to the components as shown in Table 2, the culture mediums for primary cells of intestinal cancer with combinations of different additive factors were prepared, and the proliferation-promoting effects of combinations of different additive factors on the primary cells of intestinal cancer were investigated.

TABLE 2

| Preparation of culture mediums of different components (final concentrations are shown) | |
|---|---|
| Culture Medium | Component |
| Basic Medium (BM) | DMEM/F12 + 5 μM Y27632 + 5%(v/v) fetal calf serum + 100 μg/mL Primocin |
| No. 1 | BM + 0.5 μM prostaglandin E2 + 5 nM gastrin + 200 nM A8301 + 50 μM non-essential amino acids + 5 ng/mL cholera toxin + 45 ng/mL insulin-like growth factor-1 + 25x B27 additive + 4 mM nicotinamide + 1 μg/mL insulin |
| No. 2 | No. 1 without 0.5 μM prostaglandin E2 |
| No. 3 | No. 1 without 5 nM gastrin |
| No. 4 | No. 1 without 200 nM A8301 |
| No. 5 | No. 1 without 50 μM non-essential amino acids |
| No. 6 | No. 1 without 5 ng/mL cholera toxin |
| No. 7 | No. 1 without 45 ng/mL insulin-like growth factor-1 |
| No. 8 | No. 1 without 25x B27 additive |

TABLE 2-continued

| Preparation of culture mediums of different components (final concentrations are shown) | |
|---|---|
| Culture Medium | Component |
| No. 9 | No. 1 without 4 mM nicotinamide |
| No. 10 | No. 1 without 1 μg/mL insulin |

Primary cells of intestinal cancer were obtained from intestinal cancer tissue (numbered OE0042, OE(E)006) according to the method described in step (2)-3 of Example 1, and the obtained cell suspension was divided into 11 equal parts, which were centrifuged at 1500 rpm for 4 minutes, followed by resuspending with 200 μL BM, No. 1-10 mediums, respectively. The cells were inoculated into a 48-well plate at a living cell density of $2\times10^4$ cells/cm² (20,000 cells per well), and then the plate was added with γ-ray irradiated NIH-3T3 cells (irradiation dose 30Gy) (purchased from ATCC, resuspended with Basic Medium (BM)) at a cell density of $2\times10^4$ cells/cm². Finally, each well of the 48-well plate was supplemented with the corresponding culture mediums to a volume of 1 mL, and the resultant was fully mixed. After surface disinfection, the plate was placed in a 37° C., 5% $CO_2$ incubator (purchased from Thermo Fisher) for culture.

After the cells grew to cover 85% areas or more in the 48-well plate, the mediums were discarded. The cells were rinsed with 100 μL 0.05% trypsin (purchased from Gibco) once. After the trypsin was removed, 200 μL of 0.05% trypsin was added to each well. The plate was placed in a 37° C., 5% $CO_2$ incubator for 10 minutes, and the cells were observed under a microscope (CNOPTEC, BDS400), showing that the cells had completely digested. 300 μL of DMEM/F12 medium containing 10% serum (Excell Bio, FND500) was added to stop the digestion. 20 μL of the resultant was added to a cell counting plate (Countstar, specifications: 50 pieces/box), and the total number of cells was counted with a cell counter (Countstar, IC1000). The results obtained from the primary cells of intestinal cancer isolated from intraoperative, endoscopic tissue sample OE0042, sample OE(E)006 are shown in FIG. 1.

It can be known from the results shown in FIG. 1, compared with the Basic Medium, the above No. 1-No. 10 mediums can all promote the proliferation of primary cells of intestinal cancer in different levels. When using the culture medium containing Y27632, fetal bovine serum, gastrin, A8301, non-essential amino acids, cholera toxin, insulin-like growth factor-1, B27, nicotinamide, insulin (i.e. No. 2 culture medium, hereinafter referred to as "CA-1 medium") to culture primary cells of intestinal cancer, the best proliferation effect was obtained.

Example 3. Effects of Different Concentrations of Factors Added in CA-1 Medium on the Proliferation of Primary Cells of Intestinal Cancer Primary cells of intestinal cancer were obtained from endoscopic tissue samples (numbered OE(E)042, OE(E)050, OE(E)060) according to the method described in step (2)-3 of Example 1, and the cells were cultured with CA-1 medium of Example 2. The obtained primary cells of intestinal cancer were inoculated into a 6-well plate at a living cell density of $1\times10^4$ cells/cm² (100,000 cells per well), and then the plate was added with NIH-3T3 cells irradiated by γ-ray (irradiation dose 30Gy) at a cell density of $2\times10^4$ cells/cm², and mixed well. After surface disinfection, the plate was placed in a 37° C., 5% $CO_2$ incubator (purchased from Thermo Fisher) for culture. The cells were cultured and expanded in CA-1 until growing to 85% or more. 500 μL 0.05% trypsin (purchased from Gibco) was added to rinse the cells for 1 minute. After the trypsin was removed, 500 μL 0.05% trypsin was added to each well. The plate was then placed in a 37° C., 5% $CO_2$ incubator for 2-10 minutes, until the cells was completely digested. 500 μL of DMEM/F12 medium containing 10% serum (Excell Bio, FND500) was added to stop the digestion. The resultant was centrifuged at 1500 rpm for 4 minutes, and the supernatant was discarded. The cell precipitates were resuspended using DMEM/F12, and 20 μL of suspension was added into a cell counting plate (manufacturer: Countstar, specifications: 50 pieces/box). The total number of cells was counted with a cell counter (Countstar, IC1000). The obtained cells were used for the following culture experiments.

Next, the mediums of the following 7 formulations were prepared for experiments:

Formulation 1: CA-1 medium without gastrin;
Formulation 2: CA-1 medium without A8301;
Formulation 3: CA-1 medium without non-essential amino acids;
Formulation 4: CA-1 medium without cholera toxin;
Formulation 5: CA-1 medium without insulin-like growth factor-1;
Formulation 6: CA-1 medium without B27;
Formulation 7: CA-1 medium without nicotinamide;
Formulation 8: CA-1 medium without insulin;
Formulation 9: CA-1 medium without Y-27632;
Formulation 10: CA-1 medium without fetal bovine serum.

20 μl of cell suspension containing $1 \times 10^4$ cells were added to each well, and 1 mL of the above-mentioned mediums of Formulation 1-10 were used to dilute the cell suspension, respectively.

When the medium of Formulation 1 was used, 1 mL/well of prepared gastrin was added to a 48-well plate inoculated with the primary cells at the final concentrations of gastrin of 1.25 nM, 2.5 nM, 5 nM, 10 nM, 20 nM, respectively; and the medium of Formulation 1 was used as a Blank Control (BC).

When the medium of Formulation 2 was used, 1 mL/well of prepared A8301 was added to a 48-well plate inoculated with the primary cells at the final concentrations of A8301 of 25 nM, 50 nM, 100 nM, 200 nM, 400 nM, respectively; and the medium of Formulation 2 was used as a Blank Control (BC).

When the medium of Formulation 3 was used, 1 mL/well of prepared non-essential amino acids were added to a 48-well plate inoculated with the primary cells at the final concentrations of non-essential amino acids of 25 μM, 50 μM, 100 μM, 200 μM, 400 μM, respectively; and the medium of Formulation 3 was used as a Blank Control (BC).

When the medium of Formulation 4 was used, 1 mL/well of prepared cholera toxin was added to a 48-well plate inoculated with the primary cells at the final concentrations of cholera toxin of 1.25 ng/ml, 2.5 ng/ml, 5 ng/ml, 10 ng/ml, 20 ng/ml, respectively; and the medium of Formulation 4 was used as a Blank Control (BC).

When the medium of Formulation 5 was used, 1 mL/well of prepared insulin-like growth factor-1 was added to a 48-well plate inoculated with the primary cells at the final concentrations of insulin-like growth factor-1 of 5 ng/ml, 15 ng/ml, 45 ng/ml, 135 ng/ml, 405 ng/ml, respectively; and the medium of Formulation 5 was used as a Blank Control (BC).

When the medium of Formulation 6 was used, 1 mL/well of prepared B27 was added to a 48-well plate inoculated with the primary cells at the final concentrations of B27 of 12.5×, 25×, 50×, 100×, 200×, respectively; and the medium of Formulation 6 was used as a Blank Control (BC).

When the medium of Formulation 7 was used, 1 mL/well of prepared nicotinamide was added to a 48-well plate inoculated with the primary cells at the final concentrations of nicotinamide of 1 mM, 2 mM, 4 mM, 8 mM, 16 mM, respectively; and the medium of Formulation 7 was used as a Blank Control (BC).

When the medium of Formulation 8 was used, 1 mL/well of prepared insulin was added to a 48-well plate inoculated with the primary cells at the final concentrations of insulin of 0.25 μg/ml, 0.5 μg/ml, 1 μg/ml, 2 μg/ml, 4 μg/ml, respectively; and the medium of Formulation 8 was used as a Blank Control (BC).

When the medium of Formulation 9 was used, 1 mL/well of prepared Y-27632 was added to a 48-well plate inoculated with the primary cells at the final concentrations of Y-27632 of 2.5 μM, 5 μM, 10 μM, 20 μM, 40 μM, respectively; and the medium of Formulation 9 was used as a Blank Control (BC).

When the medium of Formulation 10 was used, 1 mL/well of prepared fetal calf serum was added to a 48-well plate inoculated with the primary cells at the addition ratios of fetal calf serum of 2.5% (v/v), 5% (v/v), 10% (v/v), 20% (v/v), 40% (v/v), respectively; and the medium of Formulation 10 was used as a Blank Control (BC).

After the cells were expanded to about 85% of the 48-well plate, they were digested and counted. The proliferation multiples were calculated based on the number of cells in the Blank Control (BC), and the results were shown in FIGS. 2A-2J, respectively. In FIGS. 2A-2J, the ratio is the ratio of the number of cells obtained by culturing for the first passage using each medium to the number of cells obtained by culturing for the first passage using the corresponding Blank Control. A ratio greater than 1 indicates that the prepared medium containing different concentrations of factors or small molecular compounds has a better effect on promoting proliferation than the culture medium of the Blank Control; a ratio less than 1 indicates that the prepared medium containing different concentrations of factors or small molecular compounds has a poorer effect on promoting proliferation than the culture medium of the Blank Control.

According to the results shown in FIGS. 2A-2J, the amount of gastrin is preferably 1.25-20 nM, more preferably 2.5-10 nM, even more preferably 5 nM; the amount of A8301 is preferably 25-200 nM, more preferably 200 nM; the amount of non-essential amino acids is preferably 25-400 μM, more preferably 50 μM; the amount of cholera toxin is preferably 1.25-20 ng/ml, more preferably 2.5-5 ng/mL, even more preferably 5 ng/ml; the amount of insulin-like growth factor-1 is preferably 5-405 ng/ml, more preferably 45 ng/ml; the volume concentration of B27 is preferably 25-200×, more preferably 25-50×, even more preferably 25×; the amount of nicotinamide in the culture medium is preferably 2-8 mM, more preferably 4-8 mM, even more preferably 4 mM; the amount of insulin is preferably 0.5-4 μg/ml, more preferably 1-2 μg/mL, even more preferably 2 μg/ml; the amount of Y-27632 is preferably 2.5-40 μM, more preferably 2.5-5 μM, even more preferably 5 μM; the volume content of fetal bovine serum is preferably 2.5-5% (v/v), more preferably 5% (v/v).

Example 4. Culture and Identification of Primary Cells of Intestinal Cancer (1) Culture of Primary Cells of Intestinal Cancer According to the method described in step (2)-3 of Example 1, the primary cells of intestinal cancer were obtained from endoscopic tissue samples (numbered as OE(E)019, OE(E)028, OE(E)021, OE(E)023, OE(E)026, OE(E)025, OE(E)024, OE(E)004), and were cultured using the CA-1 medium of Example 2. The obtained primary cells of intestinal cancer were inoculated into a 6-well plate at a living cell density of $1 \times 10^4$ cells/cm$^2$ (100,000 cells per well), and then the plate was added with NIH-3T3 cells irradiated by γ-ray (irradiation dose 30Gy) at a cell density of $2 \times 10^4$ cells/cm$^2$, and mixed well. After surface disinfection, the plate was placed in a 37° C., 5% $CO_2$ incubator (purchased from Thermo Fisher) for culture.

The cultured primary cells of intestinal cancer were observed using a microscope (EVOS M500, Invitrogen). FIGS. 3A-3H are photos taken under a 10× objective lens. The cells were closely arranged and slightly irregular in shape under the microscope.

(2) Immunohistochemical Identification of Intestinal Cancer Cells Subcultured from Intestinal Cancer Tissues A cancer tissue about 0.25 cm$^3$ in size was taken from the intraoperative tissue of a patient with intestinal cancer (sample number: OE(O)001), immersed in 1 mL of 4% paraformaldehyde and fixed. Using the method of Example 3, the sample OE(O)001 was continuously cultured to the fifth passage using the medium CA-1 of the invention. Tissues or cells fixed with 4% paraformaldehyde were embedded in paraffin and cut into tissue sections of 4 μM in thickness with a microtome. Then, routine immunohistochemical assay (see Li et al., Nature Communication, (2018) 9: 2983 for specific steps) was conducted. The primary antibodies used were ki-67, CK20, CDX-2, and villin (all purchased from CST).

Figure 4:
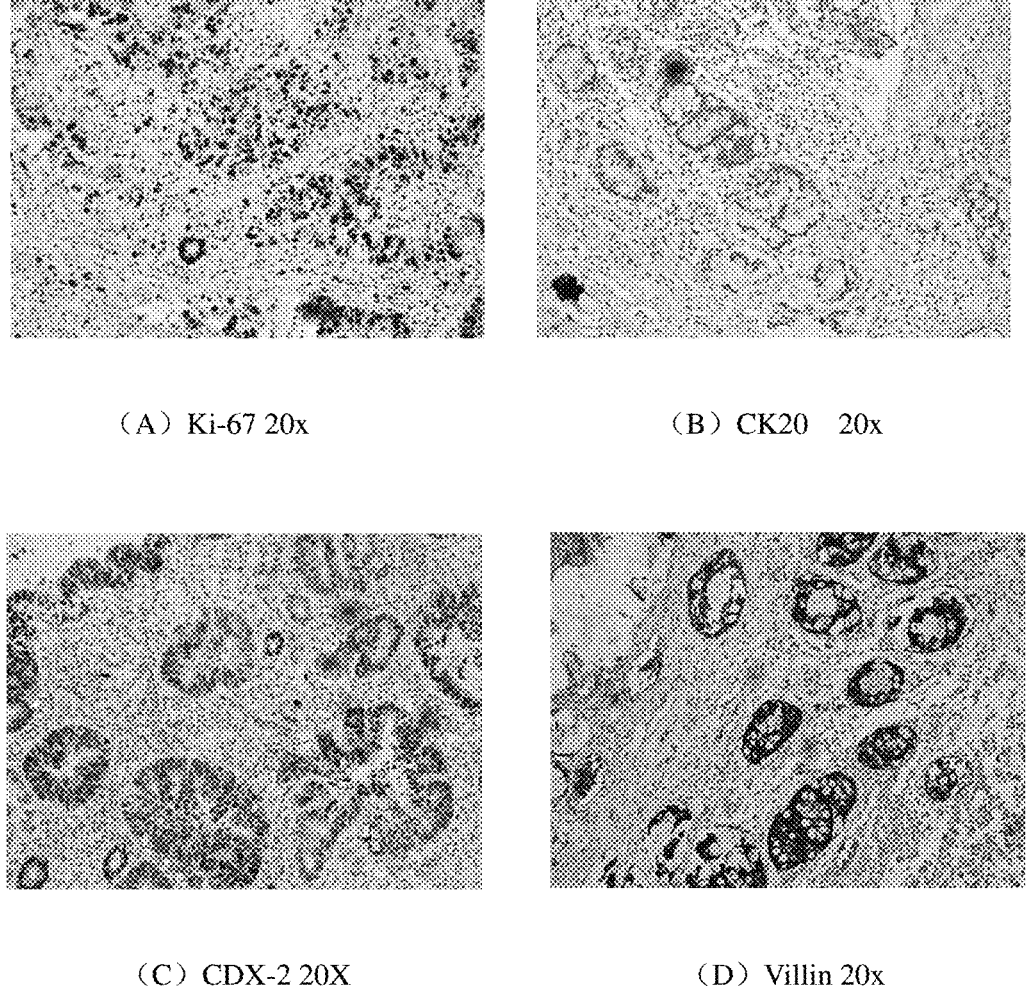
FIGS. 4A to 4D are the immunohistochemical results of cells of original intestinal cancer tissue.
Figure 5:
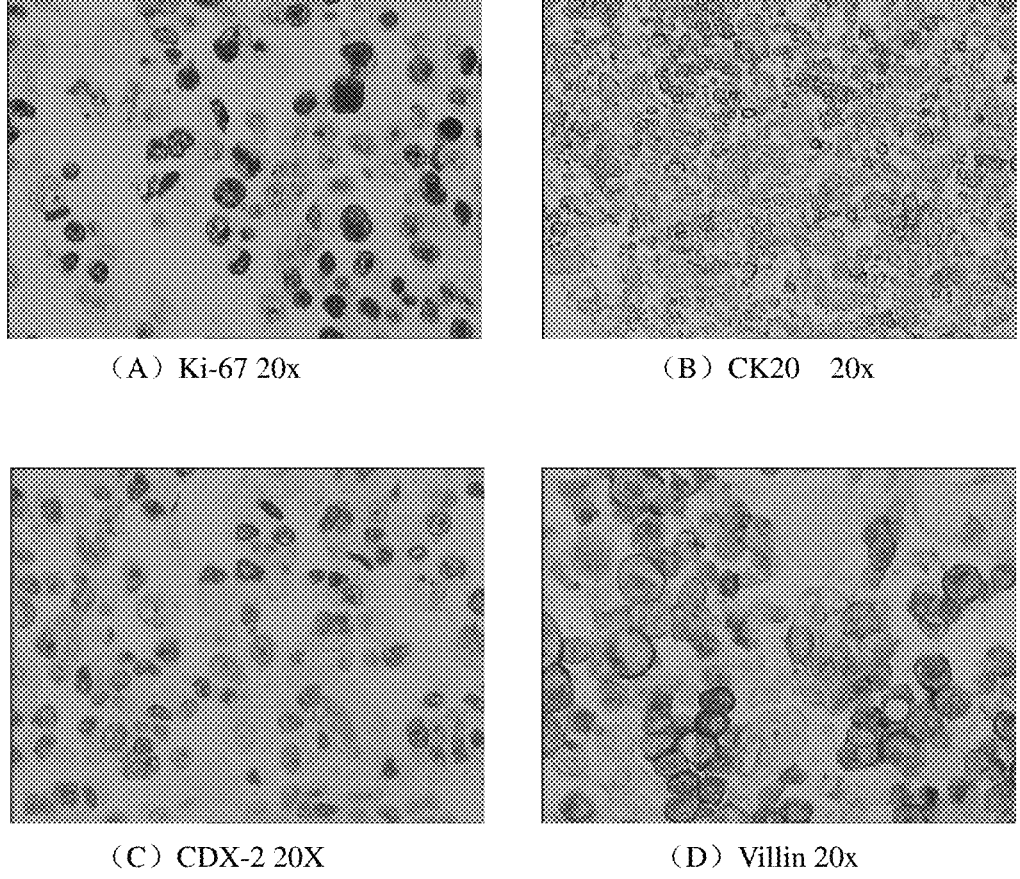
FIGS. 5A to 5D are the immunohistochemical results of primary cells of intestinal cancer cultured with the culture medium CA-1 of the invention.

FIGS. 4A-4D and 5A-5D are comparison pictures of the immunohistochemical results of original tissue cells and tumor cells of intestinal cancer obtained by culturing the original tissue cells using the medium CA-1 of the invention, respectively. FIG. 4A and FIG. 5A are pictures of intestinal cancer tissue and obtained cells after expansion and culture which were labeled with ki-67 antibody, respectively. FIG. 4B and FIG. 5B are pictures of intestinal cancer tissue and obtained cells after expansion and culture which were labeled with CK20 antibody, respectively. FIG. 4C and FIG. 5C are pictures of intestinal cancer tissue and cells obtained after expansion and culture which were labeled with CDX-2 antibody, respectively. FIG. 4D and FIG. 5D are pictures of intestinal cancer tissue and cells obtained after expansion and culture which were labeled with villin antibody, respectively. It can thus be confirmed that when the tumor cells of intestinal cancer (sample number: OE(O)001) cultured by the technology of the invention are cultured to the fifth passage, the expression of intestinal cancer-related biomarkers on the cells is basically consistent with that of the original tissue slices from which the cells were derived. It suggests that the cells cultured by the technology of the invention maintain the original pathological characteristics of the cancer tissues of patients with intestinal cancer.

(3) Immunofluorescence Identification of Primary Cells of Intestinal Cancer after Subculture The CA-1 medium of Example 2 was used to culture the sample OE(O)001 until the cells grew to 85% or more, and 500 μL of 0.05% trypsin (purchased from Gibco) was added to rinse the cells for 1 minute. After the trypsin was removed, 500 μL of 0.05% trypsin was added to each well. The plate was then placed in a 37° C., 5% $CO_2$ incubator for 2-10 minutes, until the cells were completely digested. 500 μL of DMEM/F12 medium containing 10% serum (Excell Bio, FND500) was added to stop the digestion. The resultant was centrifuged at 1500 rpm for 4 minutes, and the supernatant was discarded. The resultant was resuspended using 500 μL CA-1 medium. The cultured primary cells of intestinal cancer were identified by immunofluorescence staining.

The cultured primary cells of intestinal cancer were inoculated on cell slides (purchased from Thermo Fisher), and cultured in a 37° C., 5% $CO_2$ incubator until the cells adhered to the wall, and then cultured for another 2 to 3 days.

When the cells were expanded to cover 80% of the bottom areas, the culture medium was discarded. The resultant was washed once with PBS (purchased from Shanghai Sangon), added with 300 μL of 4% paraformaldehyde (biosharp, BL539A), and then was stand for 20 minutes at room temperature for cell fixation. The resultant was rinsed with PBS for 5 minutes, and repeated 3 times. Subsequently, PBS+0.3% Triton X-100 (purchased from Shanghai Sangon) was used to prepare a 5% volume concentration of BSA (purchased from Shanghai Sangon) solution for blocking. The blocking was performed in a water bath at 37° C. for 30 minutes. Primary antibody dilution (Beyotime, P0023A) was used to dilute antibodies, and specific antibodies ki-67, CK20, CDX-2, and villin (all purchased from CST) were diluted at a ratio of 1:50. The blocking solution was removed, and the prepared primary antibody was added. The slides were incubated overnight in a 4° C. refrigerator. Specifically, CK20 was expressed in almost all intestinal adenocarcinomas, and the colonic adenocarcinoma were identified with CDX-2(+) and villin(+).

The next day, slides were taken out from the 4° C. refrigerator and balanced to room temperature, then were incubated at 37° C. for 1 hour. Then the resultants were rinsed with PBS for 5 minutes, and repeated 3 times. Primary antibody diluent was prepared for secondary antibody dilution. Fluorescent secondary antibody (purchased from Thermo Fisher, the species was rabbit or mouse) with excitation light of 488 nm was diluted at a ratio of 1:1000, incubated at room temperature for 1 hour in the dark, rinsed with PBS for 5 minutes, and repeated 3 times.

DAPI (purchased from Sigma) was diluted in PBS at a ratio of 1:1000, stained at room temperature in the dark for 5 minutes, rinsed with PBS for 5 minutes, and repeated 3 times. Imaging was performed under a microscope (EVOS M500, Invitrogen), and photographed and recorded.

Figure 6:
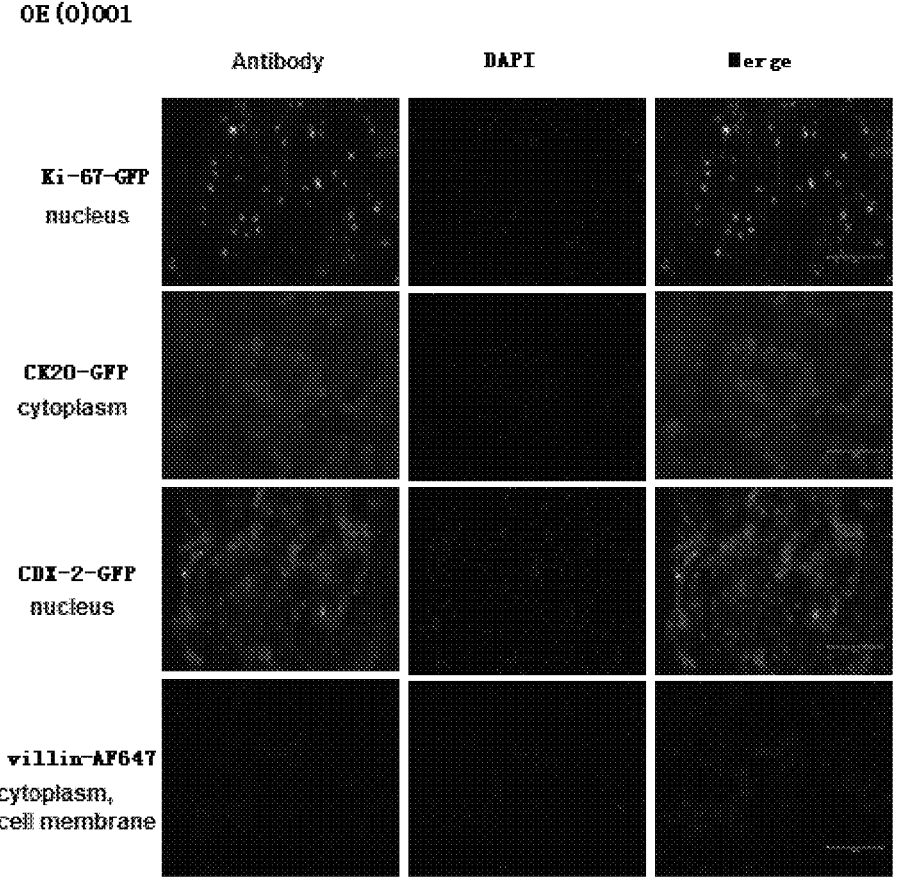
FIG. 6 shows the result of cellular immunofluorescent staining of primary cells of intestinal cancer cultured using the culture medium for primary cells of intestinal cancer of the invention.

FIG. 6 shows the results of immunofluorescence staining and identification of the primary cells of intestinal cancer cultured from sample OE(O)001 in vitro, which are the photos taken under 20× objective lens using fluorescence. As shown in FIG. 6, ki-67, CK20, CDX-2, and villin were expressed, suggesting that the sample was colorectal adenocarcinoma cells, and the diagnostic results of the primary cells cultured using the medium CA-1 of the invention were consistent with that of intestinal cancer tissue. The cells cultured using the technology of the invention maintain the original pathological characteristics of patients with intestinal cancer.

Example 5. Statistics of Initial Culture Period and Cell Number of Primary Cells of Intestinal Cancer, and Calculation of Population Doubling (PD) Value According to the method described in step (2)-3 of Example 1, primary cells of intestinal cancer were obtained from 4 cases of intestinal cancer tissue samples (numbered OE0042, OE(E)003, OE(E)006, OE(O)001). The obtained primary cells of intestinal cancer were cultured using the CA-1 medium of Example 2, and the cells were inoculated into T25 flasks at a living cell density of $2 \times 10^4$ cells/cm$^2$ and cultured. After expanded to 95%, the cells were digested and counted. At the same time, the number of days of culture until digestion was recorded as one culture period. Under this experimental condition, the cells were continuously cultured, and the obtained cells were expanded to different passages. Each passage was counted after digestion and the corresponding culture period was recorded. PD value was calculated according to the formula, Population Doubling (PD)=3.32×log 10 (total number of cells after digestion/initial number of inoculated cells). For the formula, see Chapman et al., Stem Cell Research & Therapy 2014, 5: 60.

Figure 7:
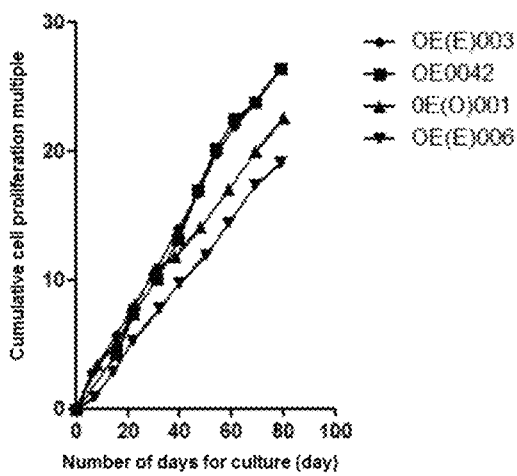
FIG. 7 shows cell growth curves of primary cells of intestinal cancer cultured with the culture medium for primary cells of intestinal cancer of the invention.

FIG. 7 shows the growth curves of 4 cases of primary cells under the culture conditions for primary cells of intestinal cancer of the invention, which were drawn by Graphpad Prism software. The abscissa represents the number of days of cell culture; the ordinate is the cumulative cell proliferation multiple, representing the multiple of cell expansion during the culture period, and the larger the value, the more multiples of cell expansion within a certain period, that is, the more cells being expanded; the slope represents the rate of cell expansion. It can be confirmed from FIG. 7 that when primary cells of intestinal cancer are continuously cultured and expanded with the medium CA-1 of the invention for at least 80 days, the cell expansion rate remains substantially unchanged and the ability to continuous expansion is still remained.

Example 6. Comparison of the Culture Effect with that of the Existing Culture Medium (1) Preparation of Culture Medium Literature medium (Xuefeng Liu et al., Nat. Protoc., 12(2): 439-451, 2017), has the formulation of: DMEM/F12 medium+250 ng/ml amphotericin B (Selleck)+10 µg/ml gentamicin (MCE)+0.1 nM cholera toxin+0.125 ng/ml EGF+25 ng/ml hydrocortisone+10 µM Y27632+10% FBS (hereinafter referred to as "LXF" medium).

(2) Obtaining and Culturing Primary Cells of Intestinal Cancer

Primary cells of intestinal cancer were obtained from intraoperative tissue samples (OE(E)003, OE0042) according to the method described in step (2)-3 of Example 1, which were then cultured with and without trophoblast cells, respectively.

When trophoblast cells were used, the cells were inoculated with the above LXF medium and CA-1 medium of Example 2 respectively, into a 48-well plate at a living cell density of $3 \times 10^4$ cells/cm$^2$ (30,000 cells per well), and then NIH-3T3 cells irradiated by γ-ray (irradiation dose 30Gy) were added at a cell density of $2 \times 10^4$ cells/cm$^2$. Finally, each well of the 48-well plate was supplemented with the corresponding culture mediums to a volume of 500 µL, and the resultant was fully mixed. After surface disinfection, the plate was placed in a 37° C., 5% CO$_2$ incubator (purchased from Thermo Fisher) for culture. After the cells grew to cover 85% areas or more in the 48-well plate, the cells were subcultured.

In case of absence of trophoblast cells, the cells were inoculated with the above LXF medium and CA-1 medium of Example 2 respectively, into a 48-well plate at a living cell density of $3 \times 10^4$ cells/cm$^2$ (30,000 cells per well), and then each well of the 48-well plate was supplemented with the corresponding culture mediums to a volume of 500 µL, and the resultant was fully mixed. After surface disinfection, the plate was placed in a 37° C., 5% CO$_2$ incubator (purchased from Thermo Fisher) for culture. After the cells grew to cover 85% areas or more in the 48-well plate, the cells were subcultured.

On the 7th day of culture, the 48-well plate was taken out, and the medium was discarded. 100 µL of 0.05% trypsin (purchased from Gibco) was used to rinse the cells once. After the trypsin was removed, 200 µL of 0.05% trypsin was added to each well. The plate was placed in a 37° C., 5% CO$_2$ incubator for 10 minutes, and the cells were observed under a microscope (CNOPTEC, BDS400) showing that the cells had completely digested. Then 300 µL of DMEM/F12 medium containing 10% serum (Excell Bio, FND500) was added to stop the digestion. 20 µL of the resultant was added to a cell counting plate (Countstar, specifications: 50 pieces/box), and the total number of cells was counted with a cell counter (Countstar, IC1000). The counting results are shown in FIGS. 8A and 8B.

Figure 8:
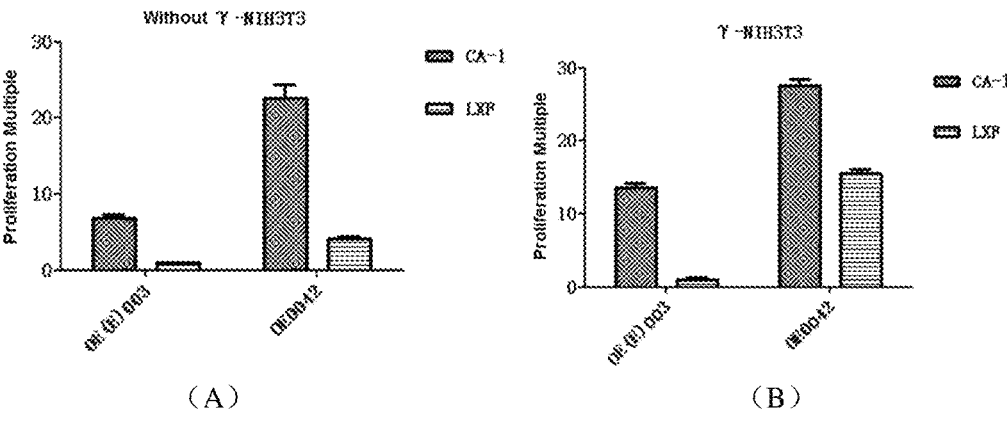
FIGS. 8A and 8B are comparison results of culture of primary cells of intestinal cancer using the culture medium CA-1 for primary cells of intestinal cancer of the invention and the existing culture medium LXF.

It can be seen from the results shown in FIGS. 8A and 8B that, compared with the LXF medium, CA-1 can significantly promote the expansion of primary cells of intestinal cancer, regardless of the presence or absence of trophoblast cells, and its effect is better than that of the LXF medium used in the prior art. Moreover, in the presence of trophoblast cells (FIG. 8B), the promotion effect on the expansion of primary cells of intestinal cancer is more significant.

Example 7. Using Primary Cells of Intestinal Cancer Obtained by Expending with the Culture Medium of the Invention for Drug Screening 1. Cell Culture and Plating According to the same method as described in Example 1, primary cells of intestinal cancer were isolated from the intestinal cancer intraoperative/endoscopic samples (OE(E) 003, OE0042) and cultured in CA-1 medium. After the cells were expanded to 85% of the plate, they were digested as one passage and then subcultured. The cells were digested and counted according to the steps described in Example 1, and the cells were placed at a living cell density of $5.76 \times 10^4$ cells/mL and mixed well in a loading slot (purchased from Corning). After being fully mixed, they were inoculated in a 384-well opaque white cell culture plate (purchased from Corning) for culture, with the volume of 50 µL per well, and the number of cells of 3000 cells/well. The plate was sealed by adding CA-1 medium from the edge of the plate, and the sample names and the testing times of CellTiter-Glo (purchased from Promega) were marked on the plate. The surface was disinfected with 75% alcohol (purchased from LIRCON), and the resultant was cultured in a 37° C., 5% CO$_2$ incubator. The first, second, third, fourth, fifth passages of the cultured cells were respectively selected for drug screening, and the drug sensitivity to the continuous passages of primary cells cultured with the medium of the invention was tested.

2. Preparation of Candidate Drugs

Two drugs (Daunorubicin and Dasatinib; both purchased from MCE) in 7 concentration gradients were prepared according to the following table, which were added to a 384-well plate (purchased from Thermo Fisher) in a volume of 30 µL per well and stored for use.

US 12,590,951 B2

15

TABLE 4

| Preparation of drug additions of Daunorubicin and Dasatinib | | | |
|---|---|---|---|
| Daunorubicin | | Dasatinib | |
| Final concentration (μM) | Preparation concentration (μM) | Final concentration (μM) | Preparation concentration (μM) |
| 1.994 | 995.5 | 0.952 | 476 |
| 0.997 | 497.75 | 0.476 | 238 |
| 0.4985 | 248.875 | 0.238 | 119 |
| 0.24925 | 124.4375 | 0.119 | 59.5 |
| 0.124625 | 62.21875 | 0.0595 | 29.75 |
| 0.0623125 | 31.109375 | 0.02975 | 14.875 |
| 0.031115625 | 15.5546875 | 0.014875 | 7.4375 |

3. High-Throughput Drug Loading

The prepared drug plates were taken out and placed at room temperature. The plates were centrifuged in a centrifuge (Beckman) at room temperature, 1000 rpm for 1 minute, and then taken out. A high-throughput automated loading system (JANUS, Perkin Elmer) was used for high-throughput drug loading. To each well of the 384-well plate with cultured cells of intestinal cancer was added 0.1 μL of the candidate drugs of corresponding concentrations. After loading the drugs, the surface of the 384-well plate was disinfected and placed into an incubator, and the cell viability was measured 72 hours later.

4. Detecting of the Cell Viability

CellTiter-Glo luminescent reagent (purchased from Promega) was taken out from a 4° C. refrigerator, and 10 mL of the reagent was added into the loading slot; the 384-well plate for testing was taken out from the incubator, and 10 μL CellTiter-Glo luminescent reagent was added into each well. After standing for 10 minutes, the test was conducted by using a multi-functional microplate reader (Envision, Perkin Elmer).

5. Data Processing

According to the formula, Cell inhibition rate (%)=100%−Chemiluminescence value of drug-loaded well/ Chemiluminescence value of control well×100%, the cell inhibition rate of cells treated with different drugs was calculated, and the half-maximal inhibitory concentration (IC50) of drugs on cells was calculated by using graphpad prism software. The results are shown in FIGS. 9A and 9B.

Figure 9:
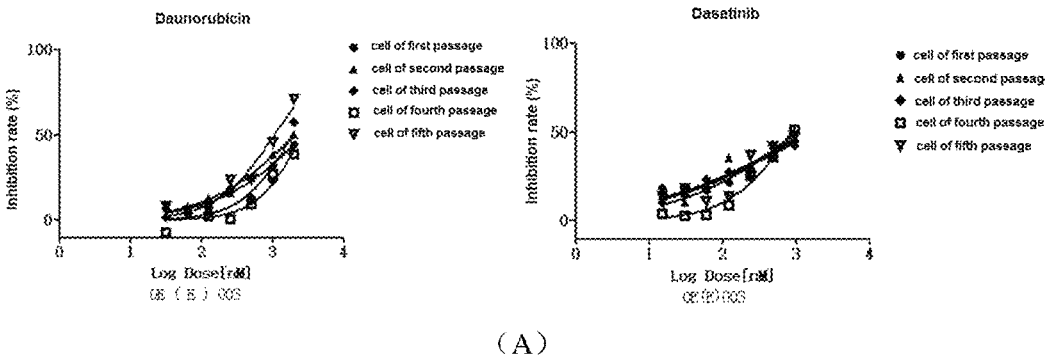
FIGS. 9A and 9B are results of drug screening using intestinal cancer cells of different generations cultured with the culture medium for primary cells of intestinal cancer of the invention.
Figure 9:
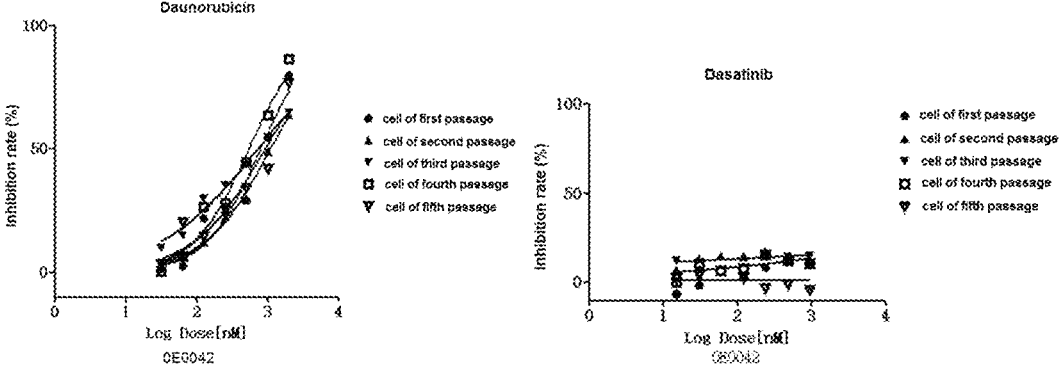

It can be confirmed from FIGS. 9A and 9B that when the intestinal cancer cells cultured by the culture medium for primary cells of intestinal cancer of the invention were used for drug screening, the inhibitory effects of the same drug on the cultured cells of different passages remain substantially the same (the inhibition curves are substantially consistent). Cells from the same patient differ in their sensitivity to different drugs at the maximum blood concentration in the human body. According to the results, the efficacy of the drug in the clinical use to the patients with intestinal cancer can be determined; and at the same time, it can be verified that the sensitivity of the tumor cells of different passages obtained according to the culture method of this patent to the drug remains stable.

INDUSTRIAL APPLICABILITY

The invention provides a culture medium and a culture method for culturing or expanding primary cells of intestinal cancer in vitro, and the cultured cells can be used in efficacy evaluating or screening of drugs. Thus, the invention is suitable for industrial applications.

Although the invention has been described in detail herein, the invention is not limited thereto, and those skilled in the art can make modifications according to the principle of the invention. Therefore, Any modification made in accordance with the principle of the invention shall be understood as falling within the protection scope of the invention.

The invention claimed is:

1. A culture medium for primary cells of intestinal cancer, comprising:
an initial culture medium, Y27632, an antibiotic, gastrin, A8301, a non-essential amino acid, cholera toxin, insulin-like growth factor-1, nicotinamide, insulin, fetal bovine serum, and B27 additive,
the initial culture medium is selected from the group consisting of Dulbecco's Modified Eagle Medium (DMEM), Ham's F-12 (F-12), DMEM/F12, and RPMI-1640, wherein,
the concentration of Y27632 is 2.5-40 μM;
the antibiotic is one or more selected from the group consisting of streptomycin/penicillin, amphotericin B and Primocin, in case of streptomycin/penicillin, with streptomycin having a concentration within the range of 25-400 μg/mL, with penicillin having a concentration within the range of 25-400 U/mL; in case of amphotericin B, having a concentration within the range of 0.25-4 μg/mL; and in case of Primocin, having a concentration within the range of 25-400 μg/mL;
the concentration of gastrin is 1.25-20 nM;
the concentration of A8301 is 25-200 nM;
the non-essential amino acid is one or more selected from the group consisting of glycine, alanine, asparagine, aspartic acid, glutamic acid, proline and serine, with a total concentration of 25-400 μM;
the concentration of cholera toxin is 1.25-20 ng/mL;
the concentration of insulin-like growth factor-1 is 5-405 ng/ml;
the concentration of nicotinamide is 2-8 mM;
the concentration of insulin is 0.5-4 μg/mL;
the volume concentration of fetal calf serum relative to the culture medium is 2.5% (v/v)-5% (v/v); and
the volume ratio of the B27 additive to the culture medium is 1:25-1:200.

2. The culture medium for primary cells of intestinal cancer of claim 1, wherein
the concentration of Y27632 is 2.5-5 μM;
the antibiotic is one or more selected from the group consisting of streptomycin/penicillin, amphotericin B and Primocin, in case of streptomycin/penicillin, with streptomycin having a concentration within the range of 50-200 μg/mL, with penicillin having a concentration within the range of 50-200 U/mL; in case of amphotericin B, having a concentration within the range of 0.5-2 μg/mL; and in case of Primocin, having a concentration within the range of 50-200 μg/mL;
the concentration of gastrin is 2.5-10 nM;
the concentration of cholera toxin is 2.5-5 ng/ml;
the concentration of nicotinamide is 4-8 mM;
the concentration of insulin is 1-2 μg/mL; and
the volume ratio of the B27 additive to the culture medium is 1:25-1:50.

3. A culture method for primary cells of intestinal cancer, comprising
culturing the primary cells of intestinal cancer in the culture medium of claim 1.

4. The culture method of claim 3, wherein the primary cells of intestinal cancer are inoculated into a culture dish at a cell density of $1\text{-}10\times10^4$ cells/cm$^2$, and trophoblast cells are added at a cell density of $2\text{-}3\times10^4$ cells/cm$^2$.

5. The culture method of claim 4, wherein the trophoblast cells are irradiated NIH-3T3 cells, the radiation source is X-ray or γ-ray, and the radiation dose is 30-50 Gy.

6. A method for screening drugs for intestinal cancer, comprising the following steps:

(1) culturing primary cells of intestinal cancer in the culture medium of claim 1;

(2) selecting a drug to be tested and diluting the drug based on the required concentration gradients;

(3) adding the drug in various concentration gradients to the cells cultured and obtained in step (1); and (4) detecting the cell viability.

7. The culture method of claim 3, wherein the concentration of Y27632 is 2.5-5 µM;

the antibiotic is one or more selected from the group consisting of streptomycin/penicillin, amphotericin B and Primocin, in case of streptomycin/penicillin, with streptomycin having a concentration within the range of 50-200 µg/mL, with penicillin having a concentration within the range of 50-200 U/mL; in case of amphotericin B, having a concentration within the range of 0.5-2 µg/mL; and in case of Primocin, having a concentration within the range of 50-200 µg/mL;

the concentration of gastrin is 2.5-10 nM;

the concentration of cholera toxin is 2.5-5 ng/ml;

the concentration of nicotinamide is 4-8 mM;

the concentration of insulin is 1-2 µg/mL; and the volume ratio of the B27 additive to the culture medium is 1:25-1:50.

8. The culture method of claim 7, wherein the primary cells of intestinal cancer are inoculated into a culture dish at a cell density of $1\text{-}10\times10^4$ cells/cm$^2$, and trophoblast cells are added at a cell density of $2\text{-}3\times104$ cells/cm$^2$.

9. The culture method of claim 8, wherein the trophoblast cells are irradiated NIH-3T3 cells, the radiation source is X-ray or γ-ray, and the radiation dose is 30-50 Gy.

10. The method of claim 6, wherein the concentration of Y27632 is 2.5-5 µM;

the antibiotic is one or more selected from the group consisting of streptomycin/penicillin, amphotericin B and Primocin, in case of streptomycin/penicillin, with streptomycin having a concentration within the range of 50-200 µg/mL, with penicillin having a concentration within the range of 50-200 U/mL; in case of amphotericin B, having a concentration within the range of 0.5-2 µg/mL; and in case of Primocin, having a concentration within the range of 50-200 µg/mL;

the concentration of gastrin is 2.5-10 nM;

the concentration of cholera toxin is 2.5-5 ng/ml;

the concentration of nicotinamide is 4-8 mM;

the concentration of insulin is 1-2 µg/mL; and the volume ratio of the B27 additive to the culture medium is 1:25-1:50.

11. The method of claim 6, wherein the primary cells of intestinal cancer are inoculated into a culture dish at a cell density of $1\text{-}10\times10^4$ cells/cm$^2$, and trophoblast cells are added at a cell density of $2\text{-}3\times10^4$ cells/cm$^2$.

12. The method of claim 11, wherein the trophoblast cells are irradiated NIH-3T3 cells, the radiation source is X-ray or γ-ray, and the radiation dose is 30-50 Gy.

13. The method of claim 10, wherein the primary cells of intestinal cancer are inoculated into a culture dish at a cell density of $1\text{-}10\times10^4$ cells/cm$^2$, and trophoblast cells are added at a cell density of $2\text{-}3\times10^4$ cells/cm$^2$.

14. The method of claim 13, wherein the trophoblast cells are irradiated NIH-3T3 cells, the radiation source is X-ray or γ-ray, and the radiation dose is 30-50 Gy.

\* \* \* \* \*